United States Patent [19]

Nielsen

[11] Patent Number: 4,746,351

[45] Date of Patent: May 24, 1988

[54] HERBICIDALLY ACTIVE SUBSTITUTED PHENOXY BENZOXAZOLE (OR BENZOTHIAZOLE)

[75] Inventor: Donald R. Nielsen, Wadsworth, Ohio

[73] Assignee: PPG Industries, Inc., Pittsburgh, Pa.

[21] Appl. No.: 861,817

[22] Filed: May 12, 1986

[51] Int. Cl.[4] .................... A01N 43/02; A01N 43/00; C07D 277/70; C07D 263/58

[52] U.S. Cl. .......................................... 71/90; 71/88; 71/92; 71/94; 544/225; 544/232; 544/337; 544/354; 546/2; 546/22; 546/270; 548/101; 548/112; 548/157; 548/159; 548/170; 548/221; 548/219; 548/165

[58] Field of Search ................. 548/221, 170, 165; 71/88, 90, 91, 97

[56] References Cited

U.S. PATENT DOCUMENTS

| 4,149,871 | 4/1979 | D'Amico | 528/165 |
|---|---|---|---|
| 4,263,440 | 4/1981 | Handte | 548/165 |
| 4,384,881 | 5/1983 | Kuyama et al. | 548/221 |
| 4,508,906 | 4/1985 | Bamberg et al. | 548/221 |
| 4,509,971 | 4/1985 | Förster et al. | 71/90 |
| 4,531,969 | 7/1985 | Nestler et al. | 548/221 |
| 4,556,411 | 12/1985 | Baum et al. | 71/90 |
| 4,571,255 | 2/1986 | Nielsen | 71/88 |
| 4,589,910 | 5/1986 | Hagen et al. | 71/90 |
| 4,594,425 | 6/1986 | Musser et al. | 548/165 |

FOREIGN PATENT DOCUMENTS

| 37524 | 10/1981 | European Pat. Off. | 548/221 |
|---|---|---|---|
| 62254 | 10/1982 | European Pat. Off. | 548/221 |
| 161602 | 10/1985 | European Pat. Off. | 548/221 |
| 171724 | 2/1986 | European Pat. Off. | 548/221 |

*Primary Examiner*—Donald G. Daus
*Assistant Examiner*—Cecilia Shen
*Attorney, Agent, or Firm*—Edward J. Whitfield

[57] ABSTRACT

This invention relates to herbicidally active substituted benzoxazole (or benzothiazole) compounds and to the use of such compounds to control the growth of noxious plants, i.e., weeds.

4 Claims, No Drawings

HERBICIDALLY ACTIVE SUBSTITUTED PHENOXY BENZOXAZOLE (OR BENZOTHIAZOLE)

FIELD OF THE INVENTION

This invention relates to herbicidally active substituted benzoxazole (or benzothiazole) compounds and to the use of such compounds to control the growth of noxious plants, i.e., weeds.

DESCRIPTION OF THE INVENTION

This invention provides herbicidally active substituted benzoxazole (or benzothiazole) compounds represented by the Formula I.

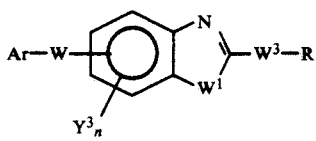

wherein Ar is

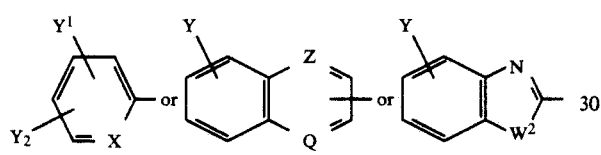

wherein:
W is oxygen, $S(O)_x$ or $NR^9$ wherein X is 0, 1 or 2 and $R^9$ is hydrogen or $C_1$ to $C_4$ alkyl;
$W^1$ and $W^2$ are independently oxygen or $S(O)_x$;
$W^3$ is oxygen or $S(O)_x$;
X is CY, N, $N^\oplus$—$O^\ominus$ or $N^\oplus$—$CH_3$;
Q is N or $N^\oplus$—$O^\ominus$;
Z is CH or N;
Y is hydrogen, halogen, cyano, nitro or lower haloalkyl;
$Y^1$ and $Y^2$ are independently hydrogen, halogen, nitro, cyano or lower alkyl, haloalkyl, alkoxy, alkoxyalkyl or alkyl sulfonyl;
$Y^3$ is hydrogen, halogen, cyano, nitro or lower haloalkyl and n is 0, 1, 2 or 3;
R is

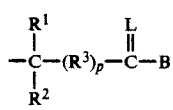

wherein
$R^1$ is hydrogen, halogen, nitro, cyano, $C_1$ to $C_4$ alkyl, haloalkyl, cycloalkyl, alkoxy or substituted alkoxy, alkoxyalkyl, carboxy, carboalkoxy, Ar, Ar—W, Ar—$R^4$ or Ar—$R^4$—W wherein $R^4$ is $C_1$ to $C_4$ alkylene;
$R^2$ is hydrogen, halogen or $C_1$ to $C_4$ alkyl;
$R^3$ is up to $C_3$ alkylene, alkenyl or alkynyl which may be mono or disubstituted by a member or members selected from $R^1$;
p is 0 or 1;
B is hydrogen, $C_1$ to $C_6$ alkyl or haloalkyl, dialkylphosphonyl, —$OR^5$, —$SR^5$ or —$NR^6R^7$ wherein:
$R^5$ is hydrogen, alkali metal, ammonium or substituted ammonium, $C_1$ to $C_6$ alkyl, haloalkyl, oxoalkyl, hydroxyalkyl, thioalkyl, alkoxyalkyl, cycloalkyl, alkylene-$S(O)_x$-alkyl, alkenyl or alkynyl, alkoxycarbonyl alkyl including amides and salts thereof, trialkylammonium alkyl, dialkylphosphonyl alkyl, $Ar^1$-$(R^8)_y$-wherein $R^8$ is $C_1$ to $C_4$ alkylene, y is 0 or 1 and $Ar^1$ is substituted or unsubstituted phenyl or pyridyl, or $R^5$ is a 5 to 6 membered heterocyclic ring containing up to 3 hetero atoms;
$R^6$ and $R^7$ are independently hydrogen, $C_1$ to $C_6$ alkyl, alkoxy, alkoxyalkyl, alkylaminoalkyl, alkylsulfonyl, dialkylphosphonyl alkyl, alkylene-$S(O)_x$-alkyl, alkenyl or alkynyl or $R^6$ and $R^7$ may combine to form a 5 to 6 membered heterocyclic ring containing up to 3 hetero atoms; and
L is oxygen or sulfur when B is —$OR^5$, —$SR^5$ or —$NR^6R^7$; but when B is hydrogen, alkyl or alkoxy L may also be dialkoxy or dioxyalkylene.

Although any herbicidally active compound within the scope of Formula I is contemplated by this invention, some preferred compounds are those represented by Formula II:

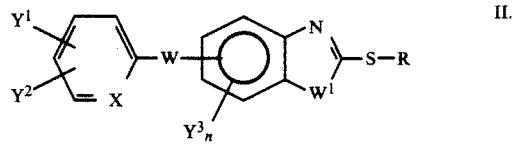

wherein X, $Y^1$, $Y^2$, $Y^3$, W, $W^1$, R and n are as previously defined.

Most preferred compounds are those Formula II compounds wherein $Y^1$ is a 2-halogen, e.g., chlorine, bromine or fluorine; $Y^2$ is a 4-lower haloalkyl, e.g., trifluoromethyl; X is CY wherein Y is hydrogen or halogen, e.g., chlorine or fluorine, W and $W^1$ are oxygen, n is 0 and R is

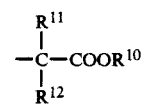

wherein $R^{11}$ and $R^{12}$ are independently hydrogen or $C_1$ to $C_4$ alkyl and $R^{10}$ is $C_1$ to $C_4$ alkyl.

Also preferred is the 5-(aryloxy)-benzoxazole isomer. Of course, the stereo isomers of the Formula I compounds are within the scope of this invention.

The compounds of the invention may be readily synthesized using methods known to the art. For example, certain of the Formula I compounds, i.e., those wherein may be prepared by reacting a suitably substituted aminophenol of the Formula III:

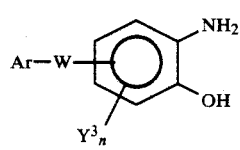

wherein Ar, W and $Y^3_n$ are as previously defined with carbon disulfide and potassium hydroxide in alcohol to form a benzoxazolethione of the Formula IV:

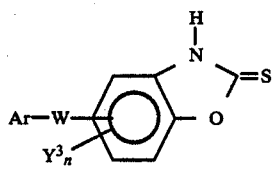

IV.

The Formula IV compound is then alkylated with a suitably substituted halogenated compound of the Formula V.

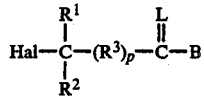

wherein Hal is halogen, e.g., bromine or chlorine, and $R^1$, $R^2$, $R^3$, p, L and B are as previously defined to form a compound of the invention.

The preparation of certain specific compounds of the invention are illustrated by the following Examples:

EXAMPLE I

Preparation of:
5-(2-chloro-4-trifluoromethylphenoxy)-2-carbomethoxymethylthiobenzoxazole A mixture of 1.73 grams (0.005 mole) of 5-(2-chloro-4-trifluoromethylphenoxy)benzoxazolethione, 20 milliliters of dimethylformamide and 1.56 grams (0.01 mole) of methyl bromoacetate was alternately stirred at room temperature and at moderate elevated temperature (43°–48° C.) over a period of several days, the progress of the reaction monitored by HPLC analysis. Upon completion of the reaction, solvent was evaporated at reduced pressure, the residue was dissolved in methylene chloride and thrice extracted with water. The organic layer was dried over anhydrous magnesium sulfate and solvent was evaporated at reduced pressure. The crude material was further purified by column chromatography using methylene chloride as the eluent, affording 0.85 grams of material identified by GC and MS analysis as the desired product.

EXAMPLE II

Preparation of:
5-(2-chloro-4-trifluoromethylphenoxy)-2-(1-carbomethoxy)ethylthiobenzoxazole A mixture of 1.73 grams (0.005 mole) of 5-(2-chloro-4-trifluoromethylphenoxy)benzoxazolethione, 1.00 gram (0.006 mole) of methyl 2-bromopropionate, 1.40 grams (0.01 mole) of potassium carbonate and 15.66 grams of dimethyl formamide was stirred at room temperature for about 24 hours, the progress of the reaction monitored by HPLC analysis. Solvent was then evaporated under reduced pressure, the residue was dissolved in methylene chloride and extracted twice with water. The organic layer was dried over anhydrous magnesium sulfate and solvent was evaporated at reduced pressure. The crude material was further purified by column chromatography using methylene chloride as the eluent, affording 1.53 grams of material confirmed by MS and HPLC analyses as the desired product.

The compounds prepared in the foregoing Examples I and II are represented by the following Formula VI:

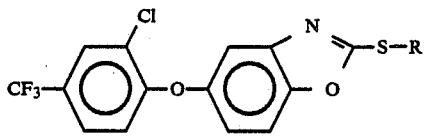

wherein R is as follows:

| Example | R |
|---------|---|
| I | —CH$_2$COOCH$_3$ |
| II | —CH(CH$_3$)COOCH$_3$ |

Although the invention has been illustrated by the foregoing Examples with regard to the preparation of specific compounds within the scope of Formula I, it is to be understood that all of other compounds within the scope of Formula I may readily be prepared by those skilled in the art by varying the choice of starting materials and using the same or similar techniques.

Weed control in accordance with this invention is effected by applying to the soil before emergence of weeds therefrom or to the plant after an emergence from the soil, a herbicidally effective amount of a compound of this invention. It is, or course, to be understood that the term "a compound of this invention" also includes mixtures of such compounds.

The term "herbicidally effective amount" is that amount of a compound of this invention required to so injure or damage weeds such that the weeds are incapable of recovering following application while not causing substantial injury to valuable crops amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Of course, the efficacy of a particular compound against a particular weed species may readily be determined by routine laboratory or field testing in a manner well known to the art. It is expected that satisfactory postemergence weed control can be had at a rate of application in the range of 0.0001 to 10 pounds per acre, and typically in the range of 0.01 to 5.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America* may be used in combination with a compound or compounds of the invention. Typically such formulations will contain from about 5 to 95 percent by weight of a compound of this invention.

The herbicidal formulations contemplated herein can be applied by any of several methods known to the art. Generally, the formulation will be applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are effective for preemergence control and particularly for postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp, nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Perennials such as quackgrass, Johnsongrass, Canada thistle, curley dock, field chickweed, dandelion, Russian knapweed aster, horsetail ironweed, seabania, cattail, wintercress, horsenettle, nutsedge, milkweed, sicklepod, and the like may also be controlled by application of the compounds of this invention.

For example, the compounds prepared in the Examples were tested for postemergence herbicidal efficacy, against a variety of broadleaf weed species, under controlled laboratory conditions of light, humidity and temperature. A solvent solution of each compound was applied to test flats containing the various weed species, and herbicidal efficacy was determined by visual inspection, periodically after application of the compounds. Herbicidal efficacy was determined on a Numerical Injury Rating (NIR) scale of from 0 (no injury) to 10 (all plants dead). A NIR rating of 7 to 9 indicates severe injury; a NIR rating of 4 to 6 indicates moderate injury, i.e., plant growth is reduced to the extent that normal growth would be expected only under ideal conditions; and a NIR rating of 1 to 3 indicates slight injury.

The following table gives the average postemergence NIR for each of the compounds of Examples I and II against the broadleaf weed species to which the compounds were applied at a rate of application of 1.0 pound per acre. The NIR was determined two weeks after application. The broadleaf weeds used in the tests were coffeeweed (COFE), jimsonweed (JMWD), tall morningglory (MNGY), teaweed (TEAW), velvetleaf (VTLF), sicklepod (SKPD) and lambsquarters (LMBQ).

|  | Postemergence NIR | |
|---|---|---|
|  | I | II |
| COFE | 5 | 10 |
| JMWD | 9 | 10 |
| MNGY | 10 | 10 |
| TEAW | 6 | 9 |
| VLTF | 6 | 10 |
| SKPD | 1 | 2 |
| LMBQ | 9 | 10 |

Although the invention has been described in considerable detail by the foregoing, it is to be understood that many variations may be made therein by those skilled in the art without departing from the spirit and scope thereof as defined by the appended claims.

What is claimed is:

1. A compound of the formula:

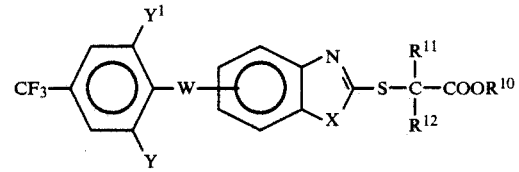

Y and $Y^1$ are independently hydrogen or halogen;
X and W are independently oxygen or sulfur; and
$R^{10}$, $R^{11}$ and $R^{12}$ are independently hydrogen or $C_1$ to $C_4$ alkyl.

2. A compound of claim 1 wherein $Y^1$ is chlorine or fluorine and Y is hydrogen, chlorine, bromine or fluorine.

3. A herbicidal formulation containing an inert carrier and a herbicidally effective amount of a compound or mixture of compounds defined by claims 1 or 2.

4. In a method of controlling weeds growth wherein a herbicidally effective amount of herbicide is applied to the situs of the weeds, the improvement residing in using as the herbicide a compound or mixture of compounds defined by claims 1 or 2.

* * * * *